| United States Patent [19] | [11] Patent Number: 4,486,416 |
| Soll et al. | [45] Date of Patent: Dec. 4, 1984 |

[54] PROTECTION OF HUMAN AND ANIMAL CELLS SUBJECT TO EXPOSURE TO TRAUMA

[76] Inventors: David B. Soll, 5001 Frankford Ave., Philadelphia, Pa. 19124; Sol E. Harrison, 1627 Buck Hill Dr., Huntingdon Valley, Pa. 19006

[21] Appl. No.: 239,791

[22] Filed: Mar. 2, 1981

[51] Int. Cl.³ .......................................... A61K 31/715
[52] U.S. Cl. ................................................... 424/180
[58] Field of Search ......................................... 424/180

[56] References Cited

U.S. PATENT DOCUMENTS

| Re. 28,093 | 7/1974 | Balassa . |
| Re. 30,239 | 3/1980 | Kuettner et al. . |
| 1,700,691 | 1/1929 | Stuart . |
| 1,950,100 | 3/1934 | Crandall . |
| 2,022,890 | 12/1935 | Livingston . |
| 2,143,475 | 1/1939 | Chase . |
| 2,187,766 | 1/1940 | Whittier . |
| 2,320,479 | 6/1943 | Sperti . |
| 2,717,227 | 9/1955 | Dawson . |
| 3,172,815 | 9/1965 | Fox et al. . |
| 3,194,732 | 7/1965 | Neuhauser . |
| 3,196,075 | 7/1965 | Neuhauser . |
| 3,211,616 | 10/1965 | Yosizawa . |
| 3,318,774 | 5/1967 | Dingwall et al. . |
| 3,329,572 | 7/1967 | Malgouzou . |
| 3,462,412 | 8/1969 | Yamada et al. . |
| 3,476,855 | 11/1969 | Balassa . |
| 3,478,146 | 11/1969 | Balassa . |
| 3,558,771 | 1/1971 | Balassa . |
| 3,624,201 | 11/1971 | Balassa . |
| 3,632,754 | 1/1972 | Balassa . |
| 3,655,416 | 4/1972 | Vinson et al. . |
| 3,672,954 | 6/1972 | Grippa . |
| 3,772,432 | 11/1973 | Balassa . |
| 3,895,106 | 7/1975 | Morrison . |
| 3,895,107 | 7/1975 | Morrison . |
| 3,903,268 | 9/1975 | Balassa . |
| 3,911,116 | 10/1975 | Balassa . |
| 3,914,413 | 10/1975 | Balassa . |
| 3,966,908 | 6/1976 | Balassa . |
| 4,094,973 | 6/1978 | Robertson . |
| 4,141,973 | 2/1979 | Balazs . |
| 4,240,163 | 12/1980 | Galin . |

OTHER PUBLICATIONS

Suyama et al.–Jap. J. Exp. Med., vol. 36, No. 4, (1966), pp. 449–452.
Kasavina et al.–Byul. Eksperim. Biol. i Med., vol. 51, No. 6, (1961), pp. 85–87, (Translation in Record).
Mishima–Am. J. Of. Ophthalmology, vol. 93, No. 1, (Jan. 1982), pp. 1–29.
Suyama et al.–Chem. Abst., vol. 66, (1967), 36462d.
Kasavina et al.–Chem. Abst., vol. 61, (1964), p. 13793a.
Drugs in Japan, Ethical Drug Edition 1975, pp. 22, 216 & English Translation of Relevant Portions.
Partridge, S. M., Davis, H. F. and Adair, G. S., "The Chemistry of Connective Tissues", Biochem. J., 79, 15, (1961).
Schroeder, H. D., Sperling, S., "Polysaccharide Coating of Human Corneal Endothelium", Acta Ophthalmologica, 55, 819–826, 1977.
Balasz, E. A., Editor, Chemistry and Molecular Biology of the Intercellular Matrix, vol. 1, 5–24, 797–821, 879–886, 921–927, 1033–1132, 1241–1253, Academic Press, London, 1970.
Langham, M. E., Hart, R. W., Cox, J., "The Interaction of Collagen and Mucopolysaccharides", Macromolecular Organization of a Connective Tissue, 157–184, Langham, M. E., Johns Hopkins Press, 1968.
Savaglio, V. P., Edelhauser, H. F., Schultz, R. O., "Corneal Polysaccharides Following Controlled-Rate Freezing, "Capella, Edelhauser, VanHorn, Corneal Preservation, 233–236, Charles C. Thomas Publisher, 1973.
Polack, F. M., Bernier, R. G., Slappey, T. E., "Sulfate Incorporation by Corneal Stoma During Cryopreservation," Capella, J. A., Edelhauser, H. F., VanHorn, D. L., Corneal Preservation, 287–293, Charles C. Thomas Publisher, 1973.
Forstor, S. L., Blackwell, W. L., Jaffe, N. S., Kaufmann, H. E., "The Effect of Intraocular Lens Implantation on the Corneal Endothelium", Trans. Amer. Acad. Ophthal., 1977.
Kanski, J. J., "Intravitreal Hyaluronic Acid Injection," British Journal of Ophthalmology, 59, 255, 1975.
Yue, B. Y. J. T., Baum, J. L., Silbert, J. E., "The Synthesis of Glycosaminoglycans by Cultures of Rabbit Corneal Endothelial and Stomal Cells," Biochem J. 158, 567–573, 1976.
Bourne, W., Kaufmann, H. E., "Endothelial Damage Associated with Intraocular Lenses", Amer. J. Ophthal., 81, 482, 1976.
Peyman, G. A., Spence, D. J., "Vital Staining of the Corneal Endothelium with Rose Bengal and Alizarin Red S.", Albrecht v. Graefes Arch klin. exp Ophthal, 201, 257, 1977.
Vrabec, F., "Studies on the Corneal and Trabecular Endothelium", Brit. J. Ophthal. 42, 529, 1958.
Nyberg, M. A., Peymann, G. A., McEnerney, J. K., "Evaluation of Donor Corneal Endothelial Viability with the Vital Stains Rose Bengal and Evans Blue", Albrecht v. Graefes Arch. Klin. exp. Ophthal., 204, 153, 1977.
Sperling, S., "Combined Staining of Corneal Endothelium by Alizarine Red and Trypane Blue", Acta Ophthal. 55, 573, 1977.

(List continued on next page.)

Primary Examiner—Sam Rosen
Attorney, Agent, or Firm—Panitch Schwarze Jacobs & Nadel

[57] ABSTRACT

Damage to endothelial and epithelial cells subject to surgery can be substantially minimized by using chondroitin sulphate. This method is particularly useful when applied prior to ophthalmic surgery, particularly intraocular lens implantation surgery.

12 Claims, No Drawings

OTHER PUBLICATIONS

Pappenheimer, A. M., "Experimental Studies Upon Lymphocytes", *J. Exp. Med.*, 25, 633, 1971.

Norn, M. S., "Pachometric Study on the Influence of Corneal Endothelial Vital Staining", *Acta Ophthal.*, 51, 679, 1973.

Knight, P. M., Link, W. J., "Surface Modification of Intraocular Lenses to Reduce Corneal Endothelial Damage", *Am. Intraocular Implant Soc. J.*, 5, 123, 1979.

Fechner, P. U., "Methylcellulose in Lens Implantation", *Am. Intraocular Implant Soc. J.*, 3, 180, 1978.

Kirk, S., Burde, R. M., Waltman, S. R., "Minimizing Corneal Endothelial Damage Due to Intraocular Lens Contact", *Invest Ophthalmol Visual Sci.* 16, 1053, 1977.

Miller, D., O'Connor, P., William, J., "Use of NaHyaluronate During Intraocular Lens Implantation in Rabbits", *Ophthalmic Surg.*, 8, 56, 1977.

Hanks, J. H., Wallace, J. H., "Determination of Cell Viability", *Proc. Soc. Exp. Biol. Med.*, 98, 188, 1958.

Schrek, R., "A Method for Counting the Viable Cells in Normal and Malignant Cell Suspensions", *Am. J. Cancer*, 28, 389, 1936.

Kaufmann, H. E., Katz, J. I., "Endothelial Damage from Intraocular Lens Insertion *Invest Ophthalmol.*, 15, 996, 1976.

Balazs, E. A., "The Molecular Biology of the Vitreous", *New and Controversial Aspects of Retinal Detachment*, 3-15, McPherson, Ed. Harper & Row, New York.

"HEALON" Product Monogram, Pharmacia Laboratories, Piscataway, N.J., 1980.

Morrison, L. M., Schjeide, O. A., *Coronary Heart Disease and the Mucopolysaccharides (Glycosaminoglycans)*, Chapter VIII, "Toxicity Studies on Acid Mucopolysaccharides", 159-169, Charles C. Thomas Publisher, Springfield, Illinois.

"Mucopolysaccharides," Encyclopedia of Biochemistry, p. 546.

Langham, Hart and Cox, "The Interaction of Collagen and Mucopolysaccharides," Macromolecular Organization of a Connective Tissue (M. Langham, Ed. 1968), p. 169.

HEALON Product Monograph, pp. 8-12, (1980).

Balazs and Gibbs, "The Rheological Properties and Biological Function of Hyaluronic Acid," Chemistry and Molecular Biology of the Intercellular Matrix (E. Balazs, Ed. 1970), p. 1250.

Miller, O'Connor and Williams, "Use of Na-Hyaluronate During Intraocular Lens Implantation in Rabbits," 8 Ophthalmic Surgery 56 (1977); p. 61.

Kishimoto, Yamanouchi, Mori and Nakamori, "Experimental Study on the Substitute of the Vitreous Body," *Acta Soc. Ophthalmol. Japan*, vol. 68, pp. 1145-1158 (1964), (English Translation Attached to Japanese Original).

S. Mori, "Experimental Study on the Substitute of the Vitreous Body, Part 2," *Acta Soc. Ophthalmol. Japan*, vol. 69, pp. 1141-1154, (1965).

PROTECTION OF HUMAN AND ANIMAL CELLS SUBJECT TO EXPOSURE TO TRAUMA

BACKGROUND OF THE INVENTION

This invention relates to a method of protecting both human and animal endothelial and epithelial cells which are subject to exposure to trauma. More particularly, this invention concerns protecting endothelial and epithelial cells in anticipation of surgical trauma using chondroitin sulphate.

Since human corneal endothelial cells are not known to reproduce, it is of vital importance to protect endothelia to prevent cell damage prior to subjection to anticipated trauma, such as surgery. Recent advances in corneal endothelial cells subject to irreversible destruction during such surgery. Of particular significance is the need to protect corneal endothelial cells during intraocular lense (IOL) implantation corneal transplantation and other intraocular surgical operations. Previous work in this field has been directed to protecting corneas with both non-biological and biological polymers.

Macromolecules heretofore employed in the protection of corneas prior to surgery include bovine serum albumin, human gamma globulin, hyaluronic acid and polyvinylpyrrolidone. The use of sodium hyaluronate as an aid in ophthalmic surgery is described in "HEALON" Product Monogram, Pharmacia Laboratories, Piscataway, N.J., 1980.

The employment of the aforementioned biological macromolecules has not met with complete satisfaction due to insufficient cell protection, i.e. significant corneal endothelial cell damage, and the onset of significant complications caused by some of these biological polymers. Sodium hyalurate, for example, is known to cause temporary glaucoma.

The therapeutic qualities of hyaluronic acid to aid wound healing have been previously reported by E. A. Balasz and D. A. Gibbs in "The Rheological Properties and Biological Function of Hyaluronic Acid", Academic Press (New York), 1970. Ultrapure hyaluronic acid and the use thereof is the subject of U.S. Pat. No. 4,141,973 to E. A. Balasz. Furthermore, it has been shown that sulphated mucopolysaccharides have a greater deturgescence effect on the cornea and that viable corneal stroma incorporate sulphur from a bath containing sulphate. See M. E. Langham, "Macromolecular Organization Of A Connective Tissue", Johns Hopkins Press, 1968; J. A. Capella, H. F. Edelhauser, D. L. Van Horn, "Corneal Preservation", Charles C. Thomas Publisher, 1973.

U.S. Pat. No. 3,211,616 of Zensaku Yosizawa concerns N,O-sulphated neutral-mucopolysaccharides.

U.S. Pat. No. 1,950,100 of Lathan A. Crandall relates to chondroitin compounds and their preparation. Crandall discloses that chondroitin is suitable for the treatment of such diseases as migraine, urticarial eruptions, peptic ulcers, multiple sclerosis, allergies and hepatic cirrhosis.

It is known that chondroitin sulphates are effective in preventing the development and evolution of some types of complicated lesions in atherosclerosis. Also the chondroitin sulphates exhibit a marked increase during various injuries to the arterial wall.

In view of the above, it would thus be advantageous to have a method which would afford significant cell protection during surgery and concomitantly be relatively free from contraindications.

SUMMARY OF THE INVENTION

There has now been discovered a method to protect both human and animal cell layers and tissues subject to exposure to trauma. This method involves administering a prophylactically effective amount of chondroitin sulphate to the anticipated site of the trauma (to the cells and tissues) prior to and/or during exposure to the trauma. Administration of an effective dosage of chondroitin sulphate is particularly useful to prevent endothelial cell damage during surgery, for example, during corneal surgery. Additionally, chondroitin sulphate can be administered after trauma as an aid in healing.

DETAILED DESCRIPTION OF THE INVENTION

Animal connective tissues contain a group of closely related acidic carbohydrate polymers which are located in the extracellular matrix and are collectively known as mucopolysaccharides. Mucopolysaccharides are heteropolysaccharides formed by the chain condensation of a pair of monomeric sugar units in an alternating sequence, and as a result, these large polymers are invariably builtup from disaccharide repeating units. One of the monomers of mucopolysaccharides is always a hexosamine (2-amino-2-deoxyglycose). The basic amino group of the hexosamine is always present as the neutral acetamido derivative.

Chondroitin sulphate has three isomers (chondrotin sulphate A, chondroitin sulphate B and chondroitin sulphate C) that are characterized by a sulphate group taking one of three positions in the repeating disaccharide unit (N-acetylchondrosin is the repeating unit). Each repeating disaccharide unit has one sulphate group.

Chondroitin sulphates A and C both contain D-glucuronic acid, 2 amino-2 deoxy-D-galactose, acetyl and sulphate residues in equimolar quantities. There is a close similarity in structure between chondroitin sulphates A and C, demonstrated by the fact that both afford the same dissacharide, chondrosine, in high yields on acidic hydrolysis. These two mucopolysaccharides are distinguished by their optical rotation and by the solubility of their calcium salts in aqueous ethanol. Chondroitin sulphates A and C structurally differ only in the position of the sulphate ester grouping in the hexosamine residue; the sulphate ester occurs at carbon-4 in the chondroitin sulphate A and carbon-6 in the chondroitin sulphate C. The nature of the hexuronic acid (L-iduronic acid) of chondroitin sulphate B serves to distinguish it form other isomeric chondroitin sulphates.

The similarity of the carbon skeleton in chondroitin sulphate B to that of chondroitin sulphate A and C is evident. In all three acid mucopolysaccharides the acid linkage is BI-3, the hexosaminidic linkage is BI-4 and the hexosamine is galactosamine.

The assignment of sulphate ester groups in chondroitin sulphates A and C to carbon-4 and carbon-6 respectively was initially based upon infrared spectral analysis, since equatorially and axially-located sulphate groups absorb at different wave lengths in the region 700–1000 $cm^{-1}$. Methylation studies have confirmed this assignment in chondroitin sulphate A.

Chondroitin sulphate B is not degraded by pneumoccal or testicular hyaluronidases and can, therefore, be distinguished from hyaluronic acid and chondroitin sulphates A and C because of this action. Its negative optical rotation ($\alpha_D = -55°$ to $-63°$) is much greater than that of chondroitin sulphate A ($\alpha_D = -28°$ to $-33°$) or chondroitin sulphate C ($\alpha_D = -16°$ to $-22°$).

Chondroitin sulphate is a sulphate acid mucopolysaccharide, which is a normal component of human cornea, and is ubiquitous in animal tissue. It is a viscous substance that has a molecular weight of about 50,000 to 100,000 depending on the source. Chondroitin sulphate is effective in the present invention at all molecular weights.

The sulphate ester content of the chondroitin sulphates is subject to wide variations depending on the source. The sulphate ester content of chondroitin sulphates in corneal extracts is usually consistently low. In contrast, the sulphate ester content of chondroitin sulphates obtained from shark connective tissues is high when compared to the sulphate ester content of chondroitin sulphates derived from equivalent mammalian sources. The degree of sulphation is not believed to have any significance in the applicability of chondroitin sulphate in the present invention.

Mucopolysaccharides are extracellular components having one or two negatively charged groups per disaccharide repeating unit. Being a sulphated mucopolysaccharide, chondroitin sulphate carries an extra negative charge per repeating unit. Chondroitin sulphate has a $-2$ charge per unit (a carbonyl group and a sulphate group each supply one negative charge). The biological macromolecule of chondroitin sulphate forms a random coiled polymer, with the repulsive forces of the negative charges maintaining a minimum volume per molecule. The polyanion itself binds many water molecules so that it forms a mucopolysaccharide water composite and generates a protective cushion.

An intraocular lense, which is manufactured from a highly electrical insulating material, strongly attracts the endothelial layer of the cornea when direct tactile contact is made. There is, in fact, an actual transfer of the endothelial cellular network, as if there were an attraction of the layer by the lense. The highly electrically conductive chondroitin sulphate arrangement is eminently suitable to eliminate this electrical attractive force. The extra negative charge associated with chondroitin sulphate also endows it with greater molecular elasticity, making it an excellent lubricating material Since acid mucopolysaccharides are viscous, highly hydrated polyanions, showing a marked degree of interaction even in dilute solution, they impede the direct flow of fluids and thus contribute to the mechanical resistance to compression. The mucopolysaccharide will limit the flow of inflammatory products, for example, proteins.

Certain bacteria, for example, staphylococcus, contain hyaluronidase An infection may spread by depolymerization, i.e. attack upon the mucopolysaccharide. Since chondroitin sulphate B does not respond to this enzyme, the use of chondroitin sulphate B would limit, or even eliminate, the activities of accidental infection during surgical procedures. Chondroitin sulphate also limits the movement of proteins and large molecules, thus aiding in the control of infection.

Another aspect of the medical benefits of chondroitin sulphate arises from the fact that certain drugs, for example, OR-Chymotripsin that are used in ocular surgery have been demonstrated to be injurious to the corneal endothelium. The chondroitin sulphate polymer, if injected into the anterior chamber of the eye, would impede the access of the chymotrypsin molecule to the endothelium.

Chondroitin sulphate can play an active as well as a passive role. Thus, it can be utilized before, during and after trauma. As a passive instrument, chondroitin sulphate physically separates tissues and acts as a lubricant. Chondroitin sulphate can also be used to float the corneal transplant.

In an active role, chondroitin sulphate behaves as a molecular sieve. It collects large molecules that participate in adhesive formation and permits the smaller molecules to permeate through it. Thus there will be an exclusion of large molecules and a space exists along each chondroitin sulphate aggregate into which no protein can move. The sieving effect acts as a hindrance to the flow of various types of molecules based on the possible entanglement of the polysaccharide chains. This leads to the development of a three dimensional network. Thus large molecules are retarded in relation to their shape, electrical charge, polar groups, etc. In certain cases chondroitin sulphate sieving can be augmented by the addition of $Ca^{2+}$ ions.

Chondroitin sulphate itself is broken down as part of the healing process. The sulphur atom of chondroitin sulphate can be radioactively traced during its incorporation into healing tissue. Chondroitin sulphate diminishes tissue rejection in tissue implants, thus acting in an active role that serves various surgical procedures including those in ophthalmology.

Chondroitin sulphate can also be utilized as a storage medium for tissue preservation, such as the overnight storage of endothelial tissue.

Although both chondroitin sulphate and "HEALON", i.e., high molecular weight (polymerized) fraction of sodium hyaluronate, are mucopolysaccharides, these two substances are quite different. "HEALON" has a much higher molecular weight than chondroitin sulphate (the molecular weight of "HEALON" is greater than 1,000,000 as compared to about 50,000 to 100,000 for chondroitin sulphate). Chondroitin sulphate does not attain the great single chain lengths of "HEALON" molecules. Chondroitin sulphate has only about 50 repeating disaccharide units per chain as compared to more than about 15,000 units per chain for "HEALON".

After ophthalmic surgery, "HEALON" remains in the anterior chamber for a very long period of time, i.e., several days. Chondroitin sulphate, however, is completely dissipated after surgery within 24 to 36 hours.

The present invention involves the utilization of chondroitin sulphate as a protective agent prior to and/or during anticipated trauma, such as surgery, to minimize or eliminate cell damage. Chondroitin sulphate may also be administered during surgery to make up any depletion occurring during surgical procedures such as vitreous loss. The use of chondroitin sulphate after surgery is effective in promoting the healing process. Of particular importance is the use of chondroitin sulphate to protect the endothelial cells of the eye prior to ophthalmic surgery such as intraocular lense insertion, intracapsular and extracapsular lense extraction, glaucoma surgery, corneal transplantation surgery, orbital surgery, extraocular muscle surgery, retinal reattachment surgery and vitreal replacement surgery. During intraocular surgery, chondroitin sulphate is very useful in reforming and maintaining the anterior chamber and the volume of the globe. The insertion of chondroitin sulphate may also serve to counter or contain vitreous bulge. Chondroitin sulphate also has use in general surgery, neurosurgery, orthopedic surgery, vascular surgery and gynecological surgery in protecting cells and maintaining body cavities and joint cavities and avoiding adhesion formations.

During, for example, cataract surgery involving intraocular lense implantation, there is a 15% to 75% loss of corneal endothelial cells depending upon the surgical trauma. A great deal of cell loss results in undue cornea swelling. Heretofore, there was no effective manner to significantly reduce such cell loss and simultaneously reduce or eliminate cornea swelling, without the occurrence of undue side-effects.

Intraocular lenses for surgical insertions come in various types and shapes. There are basically two types of intraocular lenses. One type is a compression molded intraocular lense and the other type is a lathe cut intraocular lense. Of the lathe cut type, many lense manufacturers use a methylmethacrylate known as "PERSPEX" which is a medical grade methylmathacrylate produced by Imperial Chemical Company of England. The compression molded lense types are usually made from methylmethacrylate manufactured by the Rohm & Haas Chemical Company. Chondroitin sulphate effectively guards against damage attributable to either of these two aforementioned types of methylmethacrylate lenses and the degree of protection is not dependent upon the particular shape of the lense.

The damage to cells during such surgery is generally of two kinds - mechanical and electrostatic. An exemplary protective coating for corneal surgery would thus exhibit the following attributes: the ability to absorb the impact of mechanical contact, the ability to act as a good electrical conductor (to eliminate or reduce the electrostatic interaction between the IOL and the corneal cells), high viscosity and biological compatibility. Chondroitin sulphate meets all these criteria.

All three isomer forms of chondroitin sulphate (A, B and C) can be utilized in the present invention. Chondroitin sulphate A can be derived from whale cartilage; chondroitin sulphate B can be derived from porcine skin; and chondroitin sulphate C can be derived from shark cartilage. A fairly plentiful source for chondroitin sulphate is the nasal septa of cows. Chondroitin sulphate also exists in the trachea, aorta, tendon and other parts of the animal body. Certain sections of domesticated animal cartilage contain up to 40% chondroitin sulphate by weight. All forms of chondroitin sulphate with varying sulphur contents essentially have the same mechanism of protective action and would therefore be effective in the present invention.

Chondroitin sulphate isolated from shark cartilage, and designated as chondroitin sulphate D, has revealed an infrared spectrum identical with that of chondroitin sulphate C. However, the non-identity of the two polysaccharides as acceptors in enzymatic sulphation, and the unusually high sulphur content of chondroitin sulphate D (S, 7.6%; corresponding to 1.3 sulphate residues per hexomsamine) suggests that they might be distinct species. Chondroiton sulphates from shark preparations manifest excellent properties in anterior segment surger.

A solution of chondroitin sulphate A, B or C that can be utilized in the present invention is prepared employing between 0.5% and about 30% chondroitin sulphate, preferably between about 5% and about 20%. The chondroitin sulphate in lyophylized form is reconstituted with a physiological solution such as normal saline solution and pH balanced to form a suitable treatment solution.

The chondroitin sulphate solution can be introduced to the anticipated area of the surgery by any convenient means such as using a cannula or needle, i.e., injected into a body cavity or vessel.

The chondroitin sulphate can be employed in any suitable surgical manner such as coating intraocular lenses prior to implantation and using chondroitin sulphate to form the anterior chamber in ophthalmic surgery.

TEST RESULTS

Tests were conducted in two phases: in vitro and in vivo with animals.

In Vitro Testing

The in vitro phase consisted of using animal and human corneas from enucleated eyes, and subjecting the endothelium to various staining techniques to semi-quantify endothelial damage. The amount of damage was determined after purposeful trauma with an uncoated polymethylmethacrylate lense, as compared with a lense coated with an endothelial protective substance.

The dyes used in this phase were acid violet 49 by the "dye exclusion technique" and alizarin red. "Dye exclusion technique" means the dye is rejected by the membranes of viable cells and is absorbed by cells that are damaged or necrosed.

Acid violet 49 is a sulfonated triphenylmethane compound which has been used as food dye. Large amounts of the dye have been injected intravenously without deleterious impact on animals.

Acid violet 49 is a "vital dye" which will stain the nucleus of damaged cells only. A "vital dye" is one that binds to some element of tissue without damaging it so that the tissue may continue its biologic processes. Healthy endothelial cells will not stain with acid voilet 49.

Alizarin red stains intercellular material (the "cement" between endothelial cells), thus highlighting the borders of individual endothelial cells. Alizarin red is not a "vital stain" because it damages cell membranes, as evidenced by diffuse nuclear staining with acid violet 49, after initial exposure to alizarin red. Alizarin red is useful, however, in conjunction with acid violet 49 to highlight cell borders, so long as staining with acid violet 49 is conducted first.

Alizarin red had been previously thought to be a "vital stain", a colorant for topical drugs and cosmetics, and has been frequently used without any explicit evaluation as to its vitality, or with an implied vital role. The testing demonstrated that alizarin red is not a "vital stain". The most frequent use of the dye is for calcium staining. Thus, the staining that is apparent in the intracellular "cement" may be due to the chelation of the dye and the calcuim. Simple ionic binding to macromolecules can be ruled out in this case of alizarin red, since other anionic dyes do engage in macromolecular binding, but do not exhibit any deleterious effect on the cell. Alizarin red is an anionic anthraquinone dye (3,4-hydroxy, 9,10-dioxo-2-anthracene sulfonic acid).

The combination of these two stains allows for accurate cell count of both the damaged (nucleus and border stained) and undamaged (only border stained) endothelial cells. This combination of stains thus provides for precise evaluation of endothelial viability before and after trauma, such as trauma from an IOL insertion.

Endothelial protective substances that were evaluated included: bovine serum albumin, human gamma globulin, polyvinylpyrrolidone, umbilical cord hyaluronic acid, a high molecular weight polymer salt of hyaluronic acid ("HEALON"—sodium hyaluronate) and the chondroitin sulphates. Of these substances, chondroitin sulphate was the most efficacious in preventing corneal endothelial injury.

Approximately six hundred corneas which were excised from freshly enucleated lepine, bovine, porcine, simian, canine and human eyes were utilized. The eyes were stored on damp gauze at 4° C or in plasmalyte-56 with 4.4 g CaCl2 for a short period before experimentation. Each cornea had a 2 to 3mm. rim of sclera. The corneas were placed on a "TEFLON" block and an 8 or 8.5 mm. button was trephined from each cornea after the iris was peeled off. Care was taken throughout the excision and trephination procedures not to damage the endothelium. The buttons were then placed on a glass slide with the endothelial side up for subjection to dye treatment. Due to their smaller size, the porcine corneas were not trephined; the entire porcine cornea was utilized.

The dyes alizarin red and acid violet 49 were obtained in powdered form, and purified. The acid violet 49 and the alizarin red were prepared in 10% dextrose and normal saline. Both stains were used in $10^{-2}$ and $10^{-4}$ molar solutions which were pH balanced at 7.3.

The shark chondroitin sulphate C and the umbilical cord hyaluronic acid utilized for the tests were obtained in lyophilized form, and reconstituted with normal saline which was pH balanced. The chondroitin sulphate solution contained 5 to 20 weight % chondroitin sulphate. The solution was made with physiological salt solution, to which was added 5 weight % dextrose and enough calcium to achieve a 6–12 millimolar level. The solution was pH balanced to 7.4. The bovine serum albumin and the human gamm globulin were obtained from the manufacturer in solution, diluted with normal saline, and pH balanced when necessary.

The corneal buttons were then stained with acid violet 49, rinsed with balanced salt solution, and viewed with a compound binocular microscope to check for preexisting endothelial damage. The endothelial surface of each corneal button was then subject to intraocular lense (IOL) trauma in one of three ways:
(1) gentle placement of the intraocular lense on the endothelium,
(2) gentle placement with one gentle to-and-fro movement of the intraocular lense on the endothelium,
(3) gentle placement with one more vigorous to-and-fro movement of the lense on the endothelium.

These placements were conducted by employing an iris suture IOL after one of the two iris clips had been removed. A jeweler's forceps held the IOL by the remaining iris clip. A coated IOL dipped in one of the protective solutions was placed upon the corneal endothelium surface by the forceps and moved across the cornea, taking care not to encounter the endothelium surface with either the forceps or the iris clip.

These above maneuvers were done with and without endothelial protective coatings on the IOL. If no protective coating was used, the lense was irrigated with balanced salt solution prior to endothelial contact.

Each cornea was then stained with acid violet 49, rinsed thoroughly with balanced salt solution, stained with alizarin red, and rinsed again before viewing. The staining times varied with the concentration of the dyes used: acid violet 49, $10^{-2}$ molar solution-one minute; acid violet 49, $10^{-4}$ molar solution-two minutes; alizarin red, $10^{-2}$ molar solution-two minutes; and alizarin red, $10^{-4}$ molar solution-four minutes. The endothelium was then viewed with a binocular compound microscope at various magnifications.

Several control corneas were also evaluated, following the same protocol as set forth above, except that the IOL-endothelium contact step was omitted. If all of the additional damage found after the second staining was due to the IOL interaction, these control corneas would be expected to show no additional nuclear (acid violet) staining. This was found to be true, since the staining and rinsing procedures created no visible damage.

To achieve a degree of quantitation, the damaged area in the center of each cornea was recorded and used to derive an average area of damage. The ratio of the area of damage created by the coated lenses to the average area of damage from uncoated lenses was obtained. The number of cells which had been stained before induced trauma was subtracted from the post-trauma count.

Without the use of endothelial protective substances, all methods of intraocular lense contact produced moderately severe damage (diffuse nuclear staining), or severe damage (diffuse nuclear staining with avulsion of cells). The gentle placement of the intraocular lense on the endothelium without any to-and-fro motion caused moderately severe damage in 75% of the cases, and severe damage in 25% of the cases. Any type of to-and-fro movement of the intraocular lense on the endothelium caused severe cell damage. Table 1, given hereinbelow, tabulates the damage for 57 porcine corneas showing that chondroitin sulphate manifested outstanding protective capability and was distinctly superior to the other substances tested. Albumin, umbilical cord, hyaluronic acid, and gamma globulin showed diminishing benefits, in that order. Chondroitin sulphate in concentrations of 1%, 2%, and 5% produced no damage (no nuclear staining) with gentle placement of the intraocular lense on the endothelium.

Only when both types of to-and-fro motions were employed was mild damage (patchy nuclear staining) in the greater majority of cases produced. However, in concentrations of 10% and 20%, chondriotin sulphate exerted its maximum protective effect with no damage (no nuclear staining) occurring invariably with all three types of trauma.

Acid violet 49 repeatedly demonstrated its great affinity for endothelial cells. The intensity of cellular staining seemed to correspond to the degree of endothelial injury. This was demonstrated by the observation that endothelial cells in the area of the cornea which had contact with the intraocular lens exhibited the most intense nuclear staining, with staining of the cytoplasm as well. However, the cytoplasmic staining was less intense than the nuclear staining. Areas of the cornea remote from the site of intraocular lense contact showed less intense nuclear staining without cytoplasmic staining. Thus, endothelial damage, as evidenced by the intensity of the staining with acid violet 49, appeared to be graded—the most severe damage occurring in the area of intraocular lense contact and gradually less severe damage in areas remote from the site of contact.

In Tables 2 and 3 given hereinbelow, various IOL coatings were evaluated. In Table 2, bovine corneal endoW thelium was tested; in Table 3, porcine corneal endothelium was tested. The percentage of endothelial cell damage by IOL interaction was recorded. IOL coatings utilized included chondroitin sulphate (10%, pH 6.8) bovine serum albumin (22%), gamma globulin (pH 7.2), hyaluronic acid (10%, pH 5.4) and polyvinlypyrrolidone (7%, pH 4.2). Of the IOL coatings studied, chondroitin sulphate proved to be the most effective.

In all the porcine and bovine corneas which were used for control studies, there were seventeen significant endothelial damaged corneas detected after the second staining (see Tables 2 and 3). Therefore any damage found in the corneas which had an encounter with an IOL must have been caused by this interaction and not caused by the staining technique.

The porcine and bovine data (Tables 2 and 3) demonstrated that significant damage and cell loss occurred from the interaction of the uncoated IOL and the corneal endothelium. The porcine study (Table 2) showed that eight out of the nine tested corneas suffered greater than 30% damage, while only one out of the nine corneal interactions resulted in less than 10% endothelial damage. The results of the bovine corneal data (Table 3) were also in agreement. Greater than 30% damage occurred in three of the five corneas tested with an uncoated IOL, one of the five corneas showed less than 10% damage.

The results obtained from testing bovine serum albumin, gamma globulin, polyvinylpyrrolidone, hyaluronic acid and sodium hyaluronate ("HEALON") were not as successful as the results attained by the use of chondroitin sulphate.

One-third of the porcine corneas tested with bovine serum albumin exhibited damage greater than 15% (see Table 2). Similarly, one-third of the bovine corneas tested with bovine serum albumin manifested damage greater than 20%. Bovine serum albumin also did not remain bound to the IOL, thus hampering the protection of the corneal endothelial cells.

There were five porcine corneas tested with a gamma globulin coated IOL (see Table 2). Only two of the five corneas showed less than 10% endothelial damage, none were within the less than 1% damage range.

Polyvinylpyrrolidone showed mixed results as a coating substance. The bovine corneal study (Table 3) showed that all three tested corneas were within the less than 10% damage range, however, none of the three corneas were within the 0–1% damage range. The porcine data (Table 2), however, showed only one of the three corneas tested was within the less than 10% damage range, while two of the three corneas manifested over 30% endothelial damage.

In the porcine study of fifteen corneas (Table 2), four were found to be within the 1% damage range, while the one remaining cornea was within the less than 5% damage range. In the bovine study (Table 3), five of the ten corneas tested were within the less than 1% damage range, while nine of the ten tested corneas were within the less than 5% damage range. Therefore, a total of twenty-four of the twenty-five corneas tested with chondroitin sulphate showed less than 5% endothelial damage, with the one remaining cornea exhibiting less than 1% damage. The consistent protective properties manifested by chondroitin sulphate made it the most effective IOL coating substance tested.

Four porcine corneas were tested with hyaluronic acid (Table 2) and all of these showed high damage levels of between 16–20%.

A comparison between "HEALON" (sodium hyaluronate) and chondroitin sulphate is given hereinbelow in Table 4. The eyes tested were from bovine, monkey (Rhesus and Cynomologous) and human sources. The chondroitin sulphate utilized was prepared using 20% concentration in plasmalyte-56 with 5% dextrose, pH adjusted to 7.3. As in the previous testing, chondroitin sulphate exhibited consistent protective properties. Of the twenty-two corneas tested, twenty-one manifested less than 10% endothelial damage. The protective capabilities of "HEALON" were found to be far inferior to chondroitin sulphate. None of the twenty-two tested exhibited less than 10% damage, while fourteen showed greater than 30% damage. Thus, "HEALON" is not as effective as chondroitin sulphate in protecting corneal endothelium from the damage caused by interaction with an IOL.

TABLE 1

Corneal Endothelial Damage Caused By Different Intraocular Lense Coating Materials (57 porcine corneas)

| Coating Material (weight percent) | Corneas Tested | Corneas Undamaged* | Ratio Damage** |
|---|---|---|---|
| Chondroitin sulphate (10%) | 16 | 15 | 0 |
| Bovine serum albumin (12%) | 14 | 5 | 22% |
| Umbilical cord hyaluronic acid (12%) | 15 | 2 | 41% |
| Gamma globulin | 12 | 0 | 70% |

*Undamaged corneas are defined as having fewer than ten endothelial cells damaged per 400 power field after controlled application of a coated intraocular lense.
**Ratio of damage = average area of endothelial cell damage of coated IOLs / average area of endothelial cell damage of uncoated IOLs

TABLE 2

PORCINE CORNEAL ENDOTHELIUM

| IOL COATING | TOTAL NUMBER OF CORNEAS TESTED | NUMBER OF CORNEAS TESTED SHOWING THE FOLLOWING PERCENTAGE OF ENDOTHELIAL CELLS DAMAGE BY IOL INTERACTION: | | | | | | |
|---|---|---|---|---|---|---|---|---|
| | | 0–1% | 2–5% | 6–10% | 11–15% | 16–20% | 21–30% | >30% |
| Chondroitin Sulphate | 15 | 14 | 1 | 0 | 0 | 0 | 0 | 0 |
| Bovine Serum Albumin | 24 | 9 | 1 | 6 | 0 | 3 | 2 | 3 |
| Hyaluronic Acid (Umbilical Cord Derivation) | 4 | 0 | 0 | 0 | 0 | 4 | 0 | 0 |
| Polyvinyl-pyrrolidone | 3 | 0 | 1 | 0 | 0 | 0 | 0 | 2 |

TABLE 2-continued

PORCINE CORNEAL ENDOTHELIUM

| IOL COATING | TOTAL NUMBER OF CORNEAS TESTED | NUMBER OF CORNEAS TESTED SHOWING THE FOLLOWING PERCENTAGE OF ENDOTHELIAL CELLS DAMAGE BY IOL INTERACTION: | | | | | | |
|---|---|---|---|---|---|---|---|---|
| | | 0–1% | 2–5% | 6–10% | 11–15% | 16–20% | 21–30% | >30% |
| Gamma Globulin | 5 | 0 | 1 | 1 | 1 | 1 | 0 | 1 |
| No Coating | 9 | 0 | 1 | 0 | 0 | 0 | 0 | 8 |
| Control | 4 | 4 | 0 | 0 | 0 | 0 | 0 | 0 |

TABLE 3

BOVINE CORNEAL ENDOTHELIUM

| IOL COATING | TOTAL NUMBER OF CORNEAS TESTED | NUMBER OF CORNEAS TESTED SHOWING THE FOLLOWING PERCENTAGE OF ENDOTHELIAL CELLS DAMAGE BY IOL INTERACTION: | | | | | | |
|---|---|---|---|---|---|---|---|---|
| | | 0–1% | 2–5% | 6–10% | 11–15% | 16–20% | 21–30% | >30% |
| Chondroitin Sulphate | 10 | 5 | 4 | 1 | 0 | 0 | 0 | 0 |
| Bovine Serum Albumin | 9 | 0 | 5 | 0 | 1 | 0 | 1 | 2 |
| Polyvinyl-pyrrolidone | 3 | 0 | 1 | 2 | 0 | 0 | 0 | 0 |
| No Coating | 5 | 0 | 1 | 0 | 1 | 0 | 0 | 3 |
| Control | 2 | 2 | 0 | 0 | 0 | 0 | 0 | 0 |

TABLE 4

"HEALON" VS. CHONDROITIN SULPHATE AS A PROTECTIVE COATING

| COATING SUBSTANCE | SPECIES TESTED | TOTAL NUMBER OF CORNEAS TESTED | NUMBER OF CORNEAS TESTED SHOWING THE FOLLOWING PERCENTAGE OF ENDOTHELIAL CELLS DAMAGE BY IOL INTERACTION: | | | | | | |
|---|---|---|---|---|---|---|---|---|---|
| | | | 0–1% | 2–5% | 6–10% | 11–15% | 16–20% | 21–30% | >30% |
| "HEALON" | BOVINE | 8 | 0 | 0 | 0 | 1 | 2 | 3 | 2 |
| CHONDROITIN SULPHATE | BOVINE | 9 | 6 | 2 | 1 | 0 | 0 | 0 | 0 |
| "HEALON" | MONKEY | 4 | 0 | 0 | 0 | 0 | 0 | 0 | 4 |
| CHONDROITIN SULPHATE | MONKEY | 4 | 3 | 1 | 0 | 0 | 0 | 0 | 0 |
| "HEALON" | HUMAN | 9 | 0 | 0 | 0 | 0 | 0 | 1 | 8 |
| CHONDROITING SULPHATE | HUMAN | 9 | 6 | 2 | 0 | 0 | 0 | 1 | 0 |

In Vivo Testing

The in vivo studies with animals involved the intentionally traumatic implantation of intraocular lenses (to insure endothelial touch) in rabbits and monkeys, with and without endothelial protective coatings, followed by the introduction into the anterior chamber of the vital stain acid violet 49. The only type of endothelial protective coating utilized in the in vivo testing was chondroitin sulphate. The rationale of this testing was to gauge the degree of endothelial damage by the intraocular lense or the degree of protection exerted by the intraocular lense coating substance.

Twenty monkeys (Rhesus or Cynomologous) and ten rabbits selected from New Zealand white rabbits and Dutch blackbelted rabbits were used.

Prior to cataract extraction, a 20% solution of chondroitin sulphate, prepared as described above, was injected into the anterior chamber after paracentesis to evaluate chondroitin sulphate's clearance from the chamber, its tissue compatibility, and its effect on intraocular pressure.

For each animal, the method of cataract extraction did not vary; it was performed with one peripheral iridectomy. Lense implantation was performed in one of three ways: an intraocular lense irrigated with balanced salt solution, an intraocular lense dipped in chondroitin sulphate inserted through an air filled anterior chamber, and an intraocular lense dipped in chondroitin sulphate filled anterior chamber. At the end of each procedure a solution of acid violet 49, prepared as previously described herein, was injected into the anterior chamber to highlight endothelial damage.

Since acid violet 49 has such a great affinity for damaged endothelial cells, gross examination of the intensity of corneal staining was possible in the postoperative period to judge semi-quantitatively the extent of endothelial damage. Follow-up slit-lamp biomicroscopy, and Schiotz tonometry were done at intervals in the postoperative period.

In all cases where balanced salt solution irrigation of the intraocular lense alone was used, intense violet endothelial staining with acid violet 49 was present, immediately followed hours later by corneal edema. These signs were evidence of severe endothelial damage which occurred during the traumatic IOL insertion. Intraocular lense implantation with the chondroitin sulphate coating, in an air-filled anterior chamber invariably produced no endothelial staining. The unbound dye was cleared from the anterior chamber within 12 hours. The chondroitin sulphate was no longer detectable in the anterior chamber grossly, or by slit-lamp biomicroscopy, from 24 to 35 hours postoperatively.

Filling of the anterior chamber with either chondroitin sulphate or dye generated no untoward effects. Postoperative intraocular pressures were lower than preoperative levels after the intraocular lense insertion, and returned to normal levels after one or two days. Stained damaged endothelial cells, when present, exhibited a diminished amount of staining with time. The rate or removal of the dye appeared to correlate with increasing clarity of the cornea. Several of the monkeys which received chondroitin sulphate coated IOL implants have been evaluated for over one year and no difficulties due to the implantation have been observed.

Thus, in vivo testing indicated that chondroitin sulphate is highly effective in preventing endothelial damage. The vital dye, acid violet 49, proved effective in demonstrating endothelial damage in vivo. Neither the chondroitin sulphate nor the dye had any discernible untoward effects.

The present invention may be embodied in other specific forms without departing from the spirit or essential attributes thereof and, accordingly, reference should be made to the appended claims, rather than to the foregoing specification, as indicating the scope of the invention.

We claim:

1. A method of protecting human and animal corneal endothelial cells subject to exposure to trauma, which comprises administering a prophylactically effective amount of chondroitin sulfate to said cells such that chondroitin sulfate is present during said exposure to said trauma.

2. A method according to claim 1 wherein said chondroitin sulfate is selected from the group consisting of chondroitin sulfate A, chondroitin sulfate B and chondroitin sulfate C.

3. A method according to claim 1 wherein said chondroitin sulfate is injected into the anterior chamber of the eye.

4. A method according to claim 1 wherein said trauma is surgery.

5. A method according to claim 4 wherein said surgery is intraocular lens implantation surgery.

6. A method according to claim 1 wherein said chondroitin sulfate is administered in a solution.

7. A method according to claim 1 which includes administering chondroitin sulfate during said exposure to said trauma.

8. A method according to claim 1 which includes administering chondroitin sulfate prior to said exposure to said trauma.

9. A method according to claim 1 which further comprises administering chondroitin sulfate after said exposure to said trauma.

10. A method of protecting corneal endothelial cells of a patient from the adverse effects otherwise caused by the implantation of an intraocular lens in the eye of a patient which comprises administering a prophylactically effecting amount of chondroitin sulphate such that said chondroitin sulphate is in contact with the cells and present during said implantation.

11. A method according to claim 10 wherein prior to said implantation of the intraocular lens, chondroitin sulphate is instilled into the anterior chamber of the eye to coat the cells and maintain the chamber.

12. A method according to claim 10 wherein said chondroitin sulphate is selected from the group consisting of chondroitin sulphate A, chondroitin sulphate B and chondroitin sulphate C.

* * * * *